US00PP34628P2

(12) United States Plant Patent
Krebs

(10) Patent No.: US PP34,628 P2
(45) Date of Patent: Oct. 4, 2022

(54) ***RHODODENDRON* PLANT NAMED 'HOLDENRHODO211'**

(50) Latin Name: *Rhododendron hybrida*
Varietal Denomination: HoldenRhodo211

(71) Applicant: Holden Forests and Gardens, Kirtland, OH (US)

(72) Inventor: Stephen Krebs, Painesville, OH (US)

(73) Assignee: HOLDEN FORESTS AND GARDENS, Kirtland, OH (US)

( * ) Notice: Subject to any disclaimer, the term of this patent is extended or adjusted under 35 U.S.C. 154(b) by 0 days.

(21) Appl. No.: 17/562,192

(22) Filed: Dec. 27, 2021

(51) Int. Cl.
*A01H 5/00* (2018.01)
*A01H 6/36* (2018.01)

(52) U.S. Cl.
USPC ..... Plt./238

(58) Field of Classification Search
USPC ..... Plt./226, 238
See application file for complete search history.

(56) References Cited

PUBLICATIONS

Etsy website for *Rhododendron* 'Holden'. https://www.etsy.com/listing/587225491/rhododendron-holden-pink-and-white. 2 pgs. (Year: 2020).*

* cited by examiner

*Primary Examiner* — Karen M Redden
(74) *Attorney, Agent, or Firm* — Penny J. Aguirre

(57) ABSTRACT

A new cultivar of hybrid *Rhododendron* plant named 'HoldenRhodo211' that is characterized by its resistance to root rot caused by *Phytophthora cinnamomi*, its cold hardiness at least in U.S.D.A Zone 5, its flowers that are pink in color with yellow center markings, and its adaptability to open field conditions in Northeast Ohio.

2 Drawing Sheets

Botanical classification: *Rhododendron hybrida.*
Cultivar designation: 'HoldenRhodo211'.

BACKGROUND OF THE INVENTION

The present invention relates to a new and distinct cultivar of *Rhododendron* plant of hybrid origin, botanically known as *Rhododendron* 'HoldenRhodo211' and will be referred to hereafter by its cultivar name, 'HoldenRhodo211'. 'HoldenRhodo211' is a new cultivar of *Rhododendron* shrub grown for use as a landscape plant.

The new cultivar arose from a controlled breeding program by the Inventor in Madison, Ohio and Kirtland, Ohio with the objective of developing new cultivars of *Rhododendron* with resistance to root rot, greater sun adaptability, and compact growth habits.

The new cultivar was derived from a cross made by the Inventor in spring of 1998 between *Rhododendron* 'Vernus' (not patented) as the female parent, and *Rhododendron* 'Rio' (not patented) as the male parent. The Inventor selected 'HoldenRhodo211' as a single unique plant amongst the seedlings that resulted from the above cross in winter of 2000.

Asexual propagation of the new cultivar was first accomplished by semi-hardwood stem cuttings in Madison, Ohio in fall of 2010 under the direction the Inventor. Asexual propagation by semi-hardwood stem cuttings and tissue culture utilizing meristematic tissue has determined that the characteristics of the new cultivar are stable and are reproduced true to type in successive generations.

SUMMARY OF THE INVENTION

The following traits have been repeatedly observed and represent the characteristics 'HoldenRhodo211'. These attributes in combination distinguish 'HoldenRhodo211' as a new and distinct cultivar of *Rhododendron.*

1. 'HoldenRhodo211' exhibits resistance to root rot caused by *Phytophthora cinnamomi.*
2. 'HoldenRhodo211' exhibits cold hardiness at least in U.S.D.A Zone 5.
3. 'HoldenRhodo211' exhibits flowers that are pink in color with a yellow center markings.
4. 'HoldenRhodo211' exhibits adaptability to open field conditions in Northeast Ohio.

The female parent of 'HoldenRhodo211' differs from 'HoldenRhodo211' in having an earlier blooming period and a more open growth habit. The male parent of 'HoldenRhodo211' differs from 'HoldenRhodo211' in having flowers that are a different shade of pink color and susceptibility to root rot. 'HoldenRhodo211' can also be most closely compared to the *Rhododendron* cultivars 'Haaga' (not patented) and 'Roseum Elegans' (not patented). 'Haaga' is similar to 'HoldenRhodo211' in having pink colored flowers and in being cold hardy to U.S.D.A. Zone 5. 'Haaga' differs from 'HoldenRhodo211' in being slightly more cold hardy and highly susceptible to root rot. 'Roseum Elegans' is similar to 'HoldenRhodo211' in having pink color flowers and growing well in open field conditions with low root rot disease pressure present. 'Roseum Elegans' differs from 'HoldenRhodo211' in being highly susceptible to root rot and having a larger overall plant size under commercial growing conditions.

BRIEF DESCRIPTION OF THE DRAWINGS

The accompanying color photographs illustrate the overall appearance and distinct characteristics of the new *Rho-*

*dodendron*. The plant in the photograph is 6 years in age as grown outdoors in Madison, Ohio.

Figure 1:
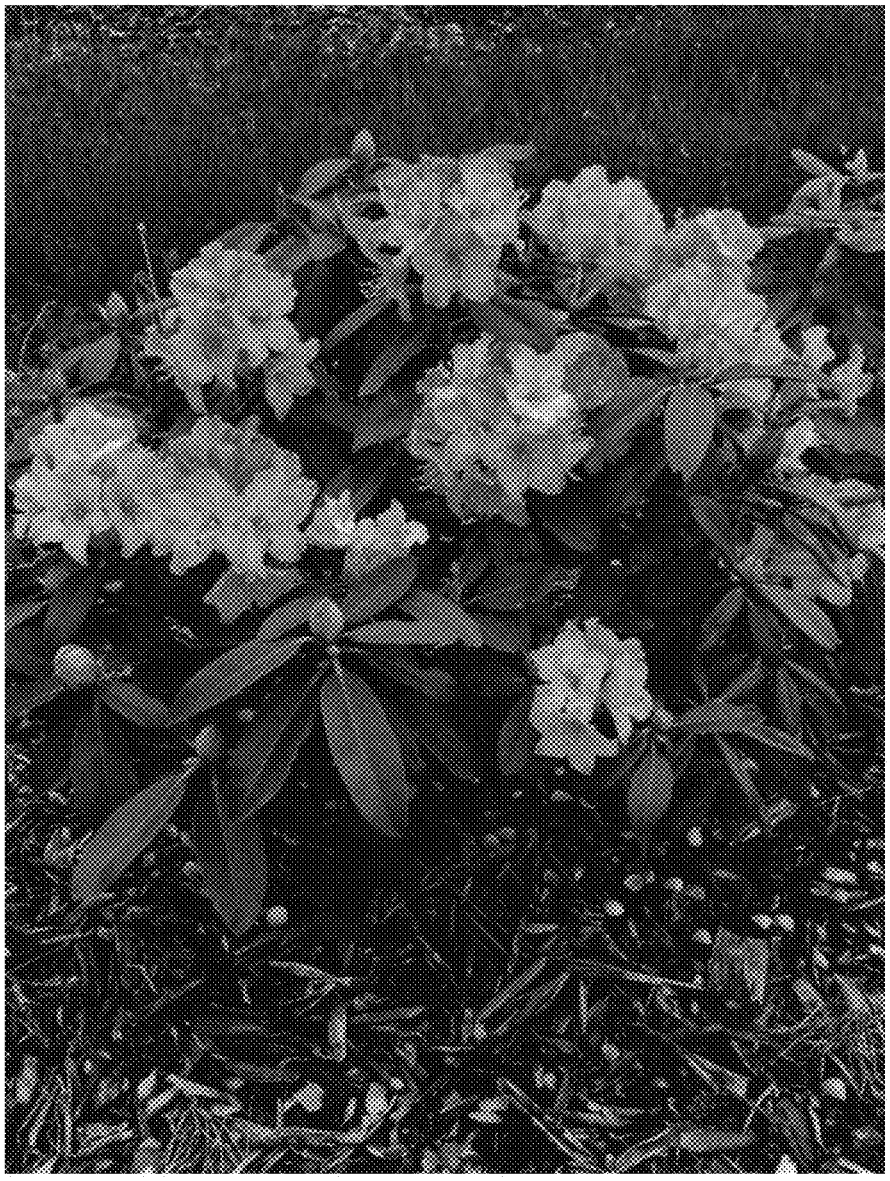

The photograph in FIG. 1 provides a view of 'HoldenRhodo211' in bloom.

Figure 2:
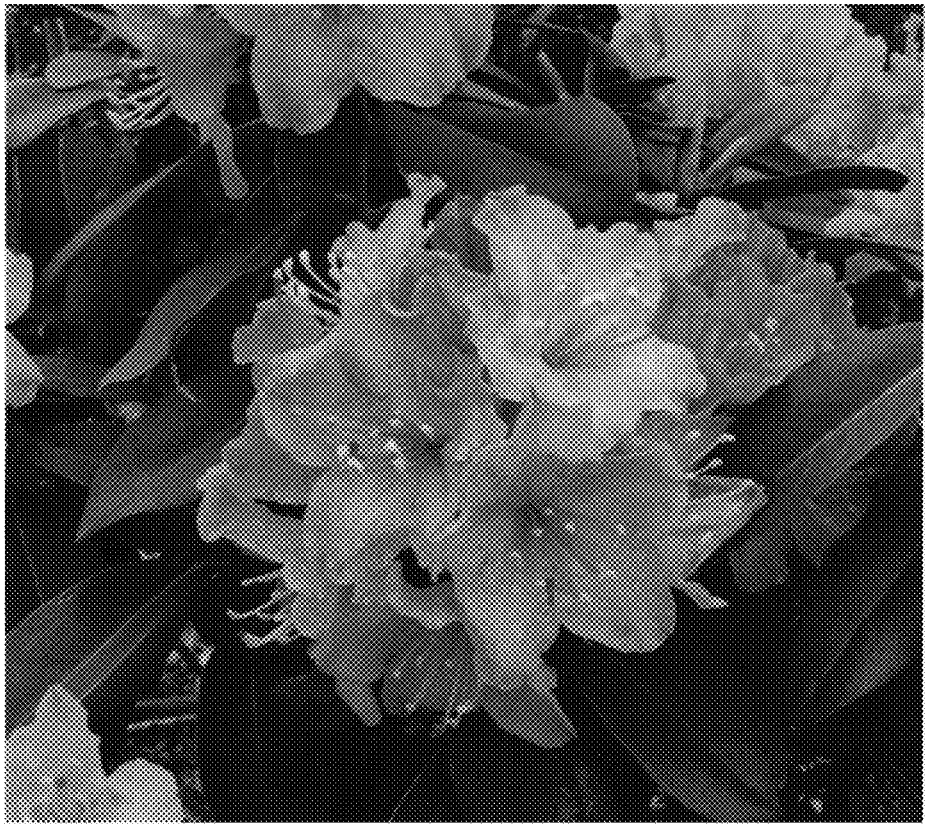

The photograph in FIG. 2 provides a close-up view of an inflorescence of 'HoldenRhodo211'.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of an 11-year-old plant of the new cultivar as grown outdoors in an evaluation garden in Madison, Ohio. The phenotype of the new cultivar may vary with variations in environmental, climatic, and cultural conditions, as it has not been tested under all possible environmental conditions. The color determination is in accordance with The 1995 Colour Chart of The Royal Horticultural Society, London, England, except where general color terms of ordinary dictionary significance are used.

General characteristics:

*Blooming period*.—2 to 3 weeks, weather dependent, typically in mid-late May in Ohio.

*Plant type*.—Evergreen shrub.

*Plant habit*.—Rounded and densely branched.

*Height and spread*.—Reaches 1 m in height and 1.3 m in width after 11 years in the landscape.

*Cold hardiness*.—Hardy to at least U.S.D.A. Zone 5a, flower buds are resistant to cold damage when exposed to temperatures of −20 F, possibly colder.

*Diseases and pests*.—Observed to be resistant to root rot caused by *Phytophthora cinnamomi* under field conditions, typical of evergreen *Rhododendrons*, lace bugs (*Stephanitis takeyai*) can establish on leaves under full sun conditions, no other susceptibility or resistance to other pests or diseases has been observed.

*Root description*.—Fibrous and near 165A in color.

*Propagation*.—Tissue culture (preferred) or semi-hardwood stem cuttings.

*Growth rate*.—Moderate.

*Root development*.—4 to 8 weeks for root initiation and 2 years to produce a young plant from a rooted cutting.

Stem description:

*Shape*.—Round.

*Stem color*.—Young; 145A, mature; a blend of 156A and 197D.

*Stem size*.—Main stem; an average of 7.5 cm in length and 5.7 cm in width, lateral branches; (previous growth); an average of 81.7 cm in length, tapering from an average of 1.66 cm in width to 5 mm in width, (current year's growth); an average of 7.1 cm in length and 5 mm in width.

*Stem surface*.—Young; mostly glabrous, covered with fine hairs less than 1 mm in length near 144C in color, mature wood; is somewhat rough, moderately exfoliating, 198B in color.

*Stem aspect*.—Held outward from main stem.

*Stem strength*.—Strong.

*Branching*.—Densely branched.

Foliage description:

*Leaf shape*.—Elliptic to obovate.

*Leaf division*.—Simple.

*Leaf base*.—Cuneate to rounded.

*Leaf apex*.—Mostly obtuse with some between acute and obtuse.

*Leaf venation*.—Pinnate, upper surface midrib near 154B in color with lateral vein color matching leaf upper surface coloration, lower surface midrib near 157A in color and lateral veins matching leaf lower surface coloration.

*Leaf margins*.—Entire.

*Leaf attachment*.—Petiolate.

*Leaf arrangement*.—Alternate, leaf clusters whorled at shoot apex.

*Leaf internode length*.—An average of 1.2 cm at its widest to 0 cm where leaves are whorled at shoot apices.

*Leaf orientation*.—Held mostly upright, some slightly downward.

*Leaf aspect*.—Leaves mostly flat, occasionally cupped downward at leaf tip.

*Leaf surface*.—Upper surface; smooth, glabrous, mildly shiny with a thick texture, lower surface; smooth, dull, glabrous.

*Leaf color*.—Young leaves upper surface; 144A with a dark yellow overtone, young leaves lower surface; 144D in color, mature leaves upper surface; a blend of 137C and 138A, mature leaves lower surface; a blend of 145A and 145B, older leaves; evergreen, occasionally turn to yellow and drop in fall.

*Leaf size*.—Ranging from 3.3 to 12.5 cm in length and 2.2 to 4.7 cm in width.

*Leaf quantity*.—An average of 5 leaves per current season shoot.

*Petioles*.—Average of 1.3 cm in length and 2 mm in diameter, near 150B in color, smooth and lightly granular pubescent surface.

Flower description:

*Inflorescence type*.—Umbellate raceme.

*Lastingness of flowers*.—Bloom duration of 2 to 3 weeks depending on weather, flower petals self-cleaning.

*Inflorescence size*.—Average of 9.1 cm in height and 9 cm in width.

*Flower size*.—An average of 3.2 cm in depth and 4.5 cm in diameter.

*Flower fragrance*.—None to very faint.

*Flower shape*.—Broad, tubular funnel.

*Flower number*.—Average of 12 per inflorescence.

*Flower aspect*.—Outward.

*Flower bud*.—Obovate in shape, 1, occasionally 2 per terminal shoot whorl, color; 151A, center stripe 153D, edges of the bud scales near 178B.

*Flower attachment*.—Pedicellate.

*Petal number*.—5.

*Petal shape*.—Ovate to elliptic.

*Petal color*.—Upper and lower surface when opening (balloon stage); 67B in color, inner surface when fully open; near 75D with 75A and 75B near apex and random areas suffused with 11C with sparse speckles of 79D, lower surface when fully open; 73B, margins 75B.

*Petal surface*.—Waxy, glabrous, and smooth on both upper and lower surfaces.

*Petal margins*.—Entire, slightly undulate.

*Petal apex*.—Acuminate and notched.

*Petal base*.—Fused.

*Petal size*.—An average of 3.5 cm in length and 2.2 cm in width.

*Sepal number*.—5.

*Sepal shape*.—Narrowly deltate.

*Sepal margin*.—Entire.

*Sepal size*.—Average of 1 mm in length and 2 mm in width.

*Sepal surface*.—Pubescent on upper and lower surface.

*Sepal apex*.—Abruptly rounded.

*Sepal base*.—Fused.

*Sepal color*.—145B on both immature and mature sepals.

*Peduncle*.—An average of 2.7 cm in height and 4 mm in diameter, 144B in color, strong, surface slightly pubescent.

*Pedicels*.—An average of 2.9 cm in length and 2 mm in diameter, 144B in color, strong, surface covered with rough, granular-pubescence 155C in color.

Reproductive organs:

*Gynoecium*.—Pistil; 1, stigmas; round in shape, 57A in color, 1 to 2 mm in diameter, style; average 3.6 cm in length, curved, color 58A near stigma to 58D near ovary, ovary; 152A in color.

*Androecium*.—Stamens; 10, anthers; oblong to elliptical in shape, 2.5 mm in length and 1.5 mm in width, 75A in color; pollen 154D in color.

*Fruit/seeds*.—Dehiscent, 5 to 6 valved capsules, size is dependent on pollination, up to 2.1 cm and 7 mm in length and width, color; interior 165C, exterior a mix of 200A, 199B, and 177B.

It is claimed:

1. A new and distinct cultivar of *Rhododendron* plant named 'HoldenRhodo211' as herein illustrated and described.

* * * * *